United States Patent
Goutsis

(10) Patent No.: US 10,045,920 B2
(45) Date of Patent: Aug. 14, 2018

(54) HAIR DYE INCLUDING DIRECT DYES AND INORGANIC BUFFER SYSTEMS

(71) Applicant: Henkel AG & Co. KGaA, Duesseldorf (DE)

(72) Inventor: Konstantin Goutsis, Juechen (DE)

(73) Assignee: Henkel AG & Co. KGaA (DE)

( * ) Notice: Subject to any disclaimer, the term of this patent is extended or adjusted under 35 U.S.C. 154(b) by 0 days.

(21) Appl. No.: 15/435,123

(22) Filed: Feb. 16, 2017

(65) Prior Publication Data

US 2017/0239152 A1     Aug. 24, 2017

(30) Foreign Application Priority Data

Feb. 22, 2016 (DE) ........................ 10 2016 202 649

(51) Int. Cl.
| | |
|---|---|
| *A61Q 5/10* | (2006.01) |
| *A61K 8/24* | (2006.01) |
| *A61K 8/46* | (2006.01) |
| *A61K 8/49* | (2006.01) |
| *A61Q 5/06* | (2006.01) |
| *A61K 8/34* | (2006.01) |
| *B65D 83/14* | (2006.01) |

(52) U.S. Cl.
CPC .................. *A61K 8/24* (2013.01); *A61K 8/34* (2013.01); *A61K 8/463* (2013.01); *A61K 8/4906* (2013.01); *A61K 8/498* (2013.01); *A61Q 5/065* (2013.01); *B65D 83/752* (2013.01); *A61K 2800/4322* (2013.01); *A61K 2800/52* (2013.01); *A61K 2800/87* (2013.01)

(58) Field of Classification Search
CPC . A61Q 5/065; A61K 8/24; A61K 8/34; A61K 8/463; A61K 8/046; B65D 83/752
See application file for complete search history.

(56) References Cited

U.S. PATENT DOCUMENTS 5,254,333 A * 10/1993 Kajino .................. A61Q 5/065
                                                                    424/70.11
6,248,314 B1    6/2001 Nakashimada et al.

FOREIGN PATENT DOCUMENTS

| | | | |
|---|---|---|---|
| GB | 2259717 A * | 7/1992 | ............... A61K 7/13 |
| GB | 2259717 A | 3/1993 | |

* cited by examiner

*Primary Examiner* — Eisa B Elhilo

(74) *Attorney, Agent, or Firm* — James J. Cummings

(57) ABSTRACT

An agent for coloring keratinic fibers, particularly human hairs, including in a cosmetic carrier (a) at least one direct dye, and (b) an inorganic butter system comprising at least one inorganic aid (b1) and at least one inorganic salt of this acid or these acids (b2), and (c) water. Further, a cosmetic product includes the aforementioned colorant which is packaged in a pressurized aerosol container possessing an aerosol dispensing device with spray valve. Finally, a method for increasing the nuance stability of colorants includes adding the aforementioned ingredients (a), (b), and (c) in the agent.

16 Claims, No Drawings

HAIR DYE INCLUDING DIRECT DYES AND INORGANIC BUFFER SYSTEMS

FIELD OF THE INVENTION

The present invention generally relates to cosmetics, and more particularly relates to agents for coloring keratinic fibers, particularly human hairs, which include at least one direct dye and one inorganic buffer system in an aqueous or water-containing carrier. These colorants are especially well suited to packaging in aerosol form. A second object of the present invention is therefore a cosmetic product comprising an agent of the first object of the invention which is packaged in a pressurized aerosol container, with the pressurized aerosol container possessing an aerosol dispensing device. A third object of the object of the present invention is a method for improving nuance stability in the coloration of keratinic fibers in which a colorant that includes at least one direct dye is mixed with an inorganic buffer system.

BACKGROUND OF THE INVENTION

The alteration of the shape and color of keratinic fibers, particularly of hairs, represents an important area of modern cosmetics. In this way, the appearance of the hairs can be adapted both to current fashion trends and to the individual desires of the individual. A person skilled in the art is familiar with various coloring systems for altering hair color depending on the coloring requirement. For permanent, intense colorations with good fastness characteristics and good gray coverage, oxidation dyeing agents are usually used. Such dyeing agents usually include oxidation dye precursors—so-called developer components and coupler components—that form the actual dyes under the influence of oxidizing agents such as hydrogen peroxide, for example. Oxidation dyeing agents are characterized by outstanding, long-lasting coloring results but are also associated with a certain degree of damage to the hair.

If the user would like to reduce hair damage or alter the hair color only temporarily, dyeing agents can be used that are based on direct dyes. In these, dyes that are already completely formed diffuse from the dyeing agent into the hair fiber. In comparison to the oxidative hair coloration, colorations obtained using direct dyes are less colorfast and wash out more quickly. Gray coverage effects that can be achieved using direct dyes also generally have room for improvement. However, the lesser damaging of the hair associated with coloration with direct dyes is advantageous.

Those skilled in the art have long known that the pH value of a hair dye can have a massive influence on the intensity of and the nuancing achieved with the coloration.

For one, the extent of the swelling of the hair depends on the pH value of the colorant. As a rule, the following applies: the more alkaline the agent applied to the hair, the greater the swelling of the hair. More pronounced swelling of the hair, in turn, promotes the diffusion of the colorants into the hair fibers. When set to higher pH values, dyes—particularly those that include neutral direct dyes (nitro dyes, for example) or cationic dyes (such as azo dyes with quaternary ammonium group, for example)—generally produce a more intense color.

Conversely, when performing coloration using acid dyes—i.e., dyes having at least one anionic charge in the form of a carboxylate or sulfonate group—an acidic pH value must usually be set in order to ensure sufficient color uptake. The color that can be achieved with acid dyes is thus generally intensified as a result of the lowering of the pH value.

The user would like to color his hair in precisely the shade that is also indicated on the packaging of the colorant. In order to achieve predictable coloration results with reproducible color intensity, is therefore essential to precisely maintain the exact pH value in the colorant.

For another, the absorption spectrum of a colorant, and hence its color, can also be influenced by the pH value. This is true of all colorants that can be protonated or deprotonated according to the principle of acid-base indicators and whose chromophoric system is influenced by corresponding protonation and deprotonation. Certain acid dyes in particular can react to slight changes in the pH value with a shift in their absorption spectrum. To achieve hair coloration with reproducible nuancing, the targeted and precise setting of the pH value is therefore also of central importance.

In principle, a person skilled in the art knows that the pH value can be adjusted in a hair dye using buffer systems. In U.S. Pat. No. 6,248,314, for example, the pH value of colorants that include not only various acid dyes but also alkylene carbonates as penetration enhancers is set using a buffer system consisting of lactic acid and caustic soda solution.

In GB 2259717 as well, colorants based on acid dyes and organic solvents are described whose pH value is buffered to a range of 3 through the use of citric acid and caustic soda solution.

In view of their long-term stability, however, none of these buffer systems known for colorants can be regarded as being optimal. Either to increase the solubility of the dyes or as penetration enhancers, most colorants based on direct dyes additionally include significant quantities of solvents (benzyl alcohols, propylene carbonates, alcohols, phenoxyethanol, etc.). It has been found that all buffer systems that are based on the use of organic acids (such as citric acid, etc.) can tend to exhibit increased crystallization particularly in these solvent-containing formulations. If a substantial portion of the buffer system crystallizes out, then it is no longer available for the acid-base equilibrium on which the buffering effect is based, and the buffer capacity can decrease.

It is therefore desirable to provide colorants based on direct dyes that can be set precisely and reproducibly to the desired pH value without encountering the drawbacks described above. The pH value of the colorants should not change, above all even over the course of extended storage.

Moreover, the pH value of the colorant should be unforeseeably influenced neither by the use of raw materials of different qualities or specifications not by the use of water of different water hardnesses.

Finally, the colorants provided in this manner should be suitable for all types of packaging, particularly including for carrier systems that include high levels of solvent, and for use in the form of an aerosol.

Furthermore, other desirable features and characteristics of the present invention will become apparent from the subsequent detailed description of the invention and the appended claims, taken in conjunction with this background of the invention.

BRIEF SUMMARY OF THE INVENTION

An agent for coloring keratinic fibers, particularly human hairs, includes in a cosmetic carrier at least one direct dye, and an inorganic buffer system comprising at least one inorganic acid (b1) and at least one inorganic salt of this acid or these acids (b2), and water.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

Surprisingly, it was found that it was possible to set the pH value of the colorants in a long-term, precise and reproducible manner if a purely inorganic buffer system, i.e., a mixture of an inorganic acid and the corresponding inorganic salt of this acid, is used to set the pH value.

Particularly in solvent-containing formulations, when purely inorganic buffer systems were used, no crystallization was observed, so that the pH value did not undergo any changes and remained stable even after several months of storage at different temperatures.

A first object of the present invention is an agent for coloring keratinic fibers, particularly human hairs, which include in a cosmetic carrier
(a) at least one direct dye, and
(b) an inorganic buffer system comprising at least one inorganic acid (b1) and at least one inorganic salt of this acid or these acids (b2), and
(c) water.

Keratinic fibers, keratin-containing fibers or keratin fibers are to be understood as furs, wool, feathers, and, particularly, human hair. Even though the agents according to the invention are suitable first and foremost for lightening and coloring keratin fibers, there is nothing in principle to prevent them from being used in other areas as well.

A characterizing feature of the agent according to the invention is its content of the essential ingredients (a), (b), and (c). As a first essential ingredient, the agent according to the invention includes at least one direct dye (a).

The direct dye(s) (a) can be preferably included in the colorant in a total quantity from 0.01 to 5.5 wt %, preferably from 0.08 to 4.7 wt %, more preferably from 0.2 to 3.4 wt %, and especially preferably from 0.3 to 1.8 wt %. The basis of calculation for the total quantity of the direct dyes (a) is the total weight of the colorant.

Direct dyes (a) can be categorized into anionic, cationic, and nonionic direct dyes. The direct dyes are preferably selected from the nitro-phenylenediamines, the nitro-aminophenols, the azo dyes, the anthraquinones, the triarylmethane dyes, or the indophenols and the physiologically acceptable salts thereof.

Dyes that carry exclusively cationic charges are usually also referred to as alkaline dyes. In the case of dyes that carry exclusively anionic charges, those skilled in the art also speak of acid dyes.

Anionic dyes react especially sensitively to changes in the pH value, so it is especially advantageous to use at least one anionic direct dye in the agents according to the invention in combination with the inorganic buffer system (b).

In an especially preferred embodiment, an agent according to the invention is characterized in that it (a) includes at least one anionic direct dye.

The terms "anionic dye" and "acid dye" are used synonymously in relation to the present invention. "Anionic dyes" and "acid dyes" are understood as being direct dyes that possess at least one carboxylic acid group (—COOH) and/or at least one sulfonic acid group (—$SO_3H$). As a function of the pH value, the protonated forms (—COOH, —$SO_3H$) of the carboxylic acid and/or sulfonic acid groups are present in equilibrium with their deprotonated forms (—$COO^-$, —$SO_3^-$). As the pH value decreases, the proportion of the protonated forms increases. If direct dyes are used in the form of their salts, then the carboxylic acid groups and/or sulfonic acid groups are present in deprotonated form and, in order to maintain electroneutrality, are neutralized with corresponding stoichiometric equivalents of cations (such as Na-cation or K-cations, for example). An anionic dye does not carry any cationic charges.

One or more compounds can be selected from the following group, for example, as suitable acid dyes: Acid Yellow 1 (D&C Yellow 7, Citronin A, Ext. D&C Yellow No. 7, Japan Yellow 403, CI 10316, COLIPA No. B001), Acid Yellow 3 (COLIPA No.: C 54, D&C Yellow No. 10, Quinoline Yellow, E104, Food Yellow 13), Acid Yellow 9 (CI 13015), Acid Yellow 17 (CI 18965), Acid Yellow 23 (COLIPA No. C 29, Covacap Jaune W 1100 (LCW), Sicovit Tartrazine 85 E 102 (BASF), Tartrazine, Food Yellow 4, Japan Yellow 4, FD&C Yellow No. 5), Acid Yellow 36 (CI 13065), Acid Yellow 121 (CI 18690), Acid Orange 6 (CI 14270), Acid Orange 7 (2-Naphthol Orange, Orange II, CI 15510, D&C Orange 4, COLIPA No. C015), Acid Orange 10 (C.I. 16230; Orange G sodium salt), Acid Orange 11 (CI 45370), Acid Orange 15 (CI 50120), Acid Orange 20 (CI 14600), Acid Orange 24 (BROWN 1; CI 20170; KATSU201; nosodiumsalt; Brown No. 201; RESORCIN BROWN; ACID ORANGE 24; Japan Brown 201; D & C Brown No. 1), Acid Red 14 (C.I.14720), Acid Red 18 (E124, Red 18; CI 16255), Acid Red 27 (E 123, CI 16185, C-Rot 46, Echtrot D, FD&C Red No. 2, Food Red 9, Naphtholrot S), Acid Red 33 (Red 33, Fuchsia Red, D&C Red 33, CI 17200), Acid Red 35 (CI C.I.18065), Acid Red 51 (CI 45430, Pyrosin B, Tetraiodfluorescein, Eosin J, Iodeosin), Acid Red 52 (CI 45100, Food Red 106, Solar Rhodamine B, Acid Rhodamine B, Red no. 106 Pontacyl Brilliant Pink), Acid Red 73 (CI 27290), Acid Red 87 (Eosin, CI 45380), Acid Red 95 (CI 45425, Erythtosine, Simacid Erythrosine Y), Acid Red 184 (CI 15685), Acid Red 195, Acid Violet 43 (Jarocol Violet 43, Ext. D&C Violet No. 2, C.I. 60730, COLIPA No. C063), Acid Violet 49 (CI 42640), Acid Violet 50 (CI 50325), Acid Blue 1 (Patent Blue, CI 42045), Acid Blue 3 (Patent Blue V, CI 42051), Acid Blue 7 (CI 42080), Acid Blue 104 (CI 42735), Acid Blue 9 (E 133, Patent Blue AE, Amido Blue AE, Erioglaucine A, CI 42090, C.I. Food Blue 2), Acid Blue 62 (CI 62045), Acid Blue 74 (E 132, CI 73015), Acid Blue 80 (CI 61585), Acid Green 3 (CI 42085, Foodgreenl), Acid Green 5 (CI 42095), Acid Green 9 (C.I.42100), Acid Green 22 (C.I.42170), Acid Green 25 (CI 61570, Japan Green 201, D&C Green No. 5), Acid Green 50 (Brilliant Acid Green BS, C.I. 44090, Acid Brilliant Green BS, E 142), Acid Black 1 (Black No. 401, Naphthalene Black 10B, Amido Black 10B, CI 20 470, COLIPA No. B15), Acid Black 52 (CI 15711), Food Yellow 8 (CI 14270), Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

In another very especially preferred embodiment, an agent according to the invention is characterized in that it (a) includes at least one anionic direct dye from the group of Acid Yellow 1, Acid Yellow 3, Acid Yellow 9, Acid Yellow 17, Acid Yellow 23, Acid Yellow 36, Acid Yellow 121, Acid Orange 6, Acid Orange 7, Acid Orange 10, Acid Orange 11, Acid Orange 15, Acid Orange 20, Acid Orange 24, Acid Red 14, Acid Red 18, Acid Red 27, Acid Red 33, Acid Red 35, Acid Red 51, Acid Red 52, Acid Red 73, Acid Red 87, Acid Red 95, Acid Red 184, Acid Red 195, Acid Violet 43, Acid Violet 49, Acid Violet 50, Acid Blue 1, Acid Blue 3, Acid Blue 7, Acid Blue 104, Acid Blue 9, Acid Blue 62, Acid Blue 74, Acid Blue 80, Acid Green 3, Acid Green 5, Acid Green 9, Acid Green 22, Acid Green 25, Acid Green 50, Acid Black 1, Acid Black 52, Food Yellow 8, Food Blue 5, D&C Yellow 7, D&C Yellow 8, D&C Orange 4, D&C Green 5, D&C Orange 10, D&C Orange 11, D&C Red 21, D&C Red 27, D&C Red 33, D&C Violet 2 and D&C Brown 1.

The acid dye(s) (a) can be preferably included in the colorant in a total quantity from 0.01 to 5.5 wt %, preferably from 0.08 to 4.7 wt %, more preferably from 0.2 to 3.4 wt %, and especially preferably from 0.3 to 1.8 wt %. The basis of calculation for the total quantity of the acid dyes is the total weight of the colorant.

The pH value of the agent according to the invention is set through the addition of an inorganic buffer system (b). In terms of the present invention, an inorganic buffer system (b) is understood as referring to a mixture of an inorganic acid (b1) and its conjugated, corresponding inorganic base (b2). A colorant that includes a buffer system according to the invention therefore includes both the inorganic acid (b1) and at least one corresponding inorganic salt of this acid (b2).

Examples of inorganic acids (b1) are sulfuric acid ($H_2SO_4$), hydrochloric acid (HCl), and phosphoric acid ($H_3PO_4$). Phosphoric acid is a medium-strong acid that is very especially preferred.

Buffer capacity can be used to determine the effectiveness of a buffer.

A buffer capacity of 1 corresponds to a buffer solution whose pH value changes by one unit upon addition of 1 mol of acid or base per liter of buffer solution.

Over the course of the work leading to the present invention, it was found that the colorants possessed an especially high buffer capacity when the acid (b1) and its corresponding salt (b2) were used in molar ratios that were optimally coordinated with one another. It is especially preferred in this connection if the inorganic acid (b1) and the salt or salts of the inorganic acid (b2) are used in a molar ratio (b1)/(b2) from 1:15 to 15:1, preferably from 1:10 to 10:1, more preferably from 1:5 to 5:1, and very especially preferably from 1:3 to 1:1.

In other words, it has been found to be most preferable if the inorganic acid (b1) and the salt or salts (b2) are either used in approximately the same total molar quantities or if the salts (b2) are included in the agent in proportion to the acid (b1) in an up to threefold molar excess.

As the basis for the calculation of the molar ratio of (b1) to (b2)—i.e., (b1)/(b2)—the total molar quantity of the inorganic acid(s) (b1) included in the agent is used, which is correlated with the total molar quantity of all of the corresponding salts (b2) included in the agent.

EXAMPLE 100 g of the agent according to the invention include, as the inorganic buffer system,
(b1) 0.9 g phosphoric acid ($H_3PO_4$) and
(b2) 1.5 g sodium dihydrogen phosphate ($NaH_2PO_4$) and 1.5 g potassium dihydrogen phosphate ($KH_2PO_4$)
molar mass of phosphoric acid ($H_3PO_4$)=97.95 g/mol
molar mass of sodium dihydrogen phosphate ($NaH_2PO_4$)= 119.92 g/mol
molar mass of potassium dihydrogen phosphate ($KH_2PO_4$)= 136.032 g/mol
100 g of the agent according to the invention include
(b1) 0.00918 mol phosphoric acid (=9.2 mmol) and
(b2) 0.0125 mol sodium dihydrogen phosphate (12.5 mmol) and 0.011 mol (11.0 mmol) potassium dihydrogen phosphate The average molar ratio (b1)/(b2) is [(0.00918 mol)/ (0.0125 mol+0.011 mol)]= 0.00918 mol/0.0235]=1:2.6

In another very especially preferred embodiment, an agent according to the invention is characterized in that the inorganic acid (b1) and the salt or salts of the inorganic acid (b2) are included in a molar ratio (b1)/(b2) from 1:15 to 15:1, preferably from 1:10 to 10:1, more preferably from 1:5 to 5:1, and very especially preferably from 1:3 to 1:1.

The pH value to which the agent according to the invention is set is dependent on the quantity of inorganic acid used in the agent. It was found that good results were obtained particularly if the agent includes—in relation to its total weight—one or more inorganic acids (b1) in a total quantity from 0.1 to 5.0 wt %, preferably from 0.3 to 2.5 wt %, more preferably from 0.4 to 1.8 wt %, and very especially preferably from 0.5 to 1.2 wt %.

In another very especially preferred embodiment, an agent according to the invention is characterized in that it includes—with respect to the total weight of the agent—(b1) one or more inorganic acids in a total quantity from 0.1 to 5.0 wt %, preferably 0.3 to 2.5 wt %, more preferably 0.4 to 1.8 wt % and very especially preferably 0.5 to 1.2 wt %.

The fine adjustment of the pH value, the buffer capacity, and the stability of the pH value continue to be influenced substantially by the quantity used of the corresponding salts (b2) of the inorganic acid. In this connection, it was especially advantageous if the agent according to the invention includes—with respect to its total weight—one or more salts (b2) of the inorganic acid(s) in a total quantity from 0.1 to 5.0 wt %, preferably from 0.4 to 4.0 wt %, more preferably from 0.5 to 3.5 wt %, and very especially preferably from 1.0 to 3.2 wt %.

In another very especially preferred embodiment, an agent according to the invention is characterized in that it includes—with respect to the total weight of the agent—(b2) one or more salts of the inorganic acid(s) in a total quantity from 0.1 to 5.0 wt %, preferably 0.4 to 4.0 wt %, more preferably 0.5 to 3.5 wt % and very especially preferably 1.0 to 3.2 wt %.

Phosphate buffer was found to be a very especially well suited inorganic buffer system (b): Phosphoric acid dissociates over three stages:

$H_3PO_4 + H_2O \rightleftharpoons H_2OP_4^- + H_3O^+$  pKa1=2.0

$H_2PO_4^- + H_2O \rightleftharpoons HPO_4^{2-} + H_3O^+$  pKa2=7.2

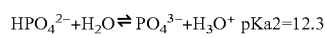

$HPO_4^{2-} + H_2O \rightleftharpoons PO_4^{3-} + H_3O^+$  pKa2=12.3

The three pK values of the phosphonic acid make it clear that proton donation becomes more difficult after each stage. $H_3PO_4$ is a medium-strong acid, whereas $H_2PO_4$ is a weak acid and $HPO_4^{2-}$ is a very weak acid.

In terms of the present invention, a phosphate buffer is especially preferably understood as an inorganic buffer system which includes
(b1) phosphoric acid ($H_3PO_4$) and
(b2) at least one inorganic phosphate salt from the group of potassium dihydrogen phosphate ($KH_2PO_4$), sodium dihydrogen phosphate ($NaH_2PO_4$), dipotassium hydrogen phosphate ($K_2HPO_4$), disodium hydrogen phosphate ($Na_2HPO_4$), potassium phosphate ($K_3PO_4$), and sodium phosphate ($Na_3PO_4$).

The quantity and type of the salts (b2) will be chosen by the person skilled in the art as a function of the exact pH value desired.

The use of the phosphate buffer has been found to be suitable particularly for setting pH values in the acidic range. In the acidic range, starting from phosphoric acid ($H_3PO_4$), a first dissociation to the dihydrogen phosphate salt ($H_2PO_4^-$) occurs, so that particularly the phosphoric acid is present in equilibrium with the corresponding dihydrogen phosphate salt at these acidic pH values.

It is therefore explicitly very especially preferred to use
(b1) phosphoric acid ($H_3PO_4$) and
(b2) at least one phosphate salt from the group of potassium dihydrogen phosphate ($KH_2PO_4$) and sodium dihydrogen phosphate ($NaH_2PO_4$).

An agent for coloring keratinic fibers, particularly human hairs, is therefore very especially preferred which includes, in a cosmetic carrier,
(a) at least one anionic direct dye and
(b1) phosphoric acid ($H_3PO_4$) and
(b2) at least one phosphate salt from the group of potassium dihydrogen phosphate ($KH_2PO_4$) and sodium dihydrogen phosphate ($NaH_2PO_4$) and
(c) water.

In other words, an agent for coloring keratinic fibers, particularly human hairs, is therefore very especially preferred which includes, in a cosmetic carrier,
(a) at least one anionic direct dye and
(b2) an inorganic buffer system comprising (b1) phosphoric acid ($H_3PO_4$) and at least one phosphate salt from the group of potassium dihydrogen phosphate ($KH_2PO_4$) and sodium dihydrogen phosphate ($NaH_2PO_4$) and
(c) water.

In particular, (b1) phosphoric acid ($H_3PO_4$) and (b2) potassium dihydrogen phosphate ($KH_2PO_4$) and/or sodium dihydrogen phosphate ($NaH_2PO_4$) are especially preferably used in certain molar ratios (b1)/(b2) with respect to one another which lie in the range from 1:5 to 5:1, preferably from 1:3 to 3:1, and especially preferably from 1:3 to 1:1.

Here again, the basis for the calculation of the molar ratio of (b1) to (b2)—i.e., (b1)/(b2)—is the total molar quantity of the inorganic acid (b1) included in the agent, which is correlated with the total molar quantity of all of the corresponding salts (b2) included in the agent.

In another especially preferred embodiment, an agent according to the invention for coloring keratinic fibers is characterized in that it includes an inorganic buffer system comprising
(b1) phosphoric acid ($H_3PO_4$) and
(b2) at least one phosphate salt from the group of potassium dihydrogen phosphate ($KH_2PO_4$) and sodium dihydrogen phosphate ($NaH_2PO_4$),
   with the agent that includes the inorganic acid (b1) and the salt or salts of the inorganic acid (b2) are used in a molar ratio (b1)/(b2) from 1:5 to 5:1, preferably from 1:3 to 3:1, and especially preferably from 1:3 to 1:1.

An agent for coloring keratinic fibers, particularly human hairs, is therefore very especially preferred which includes, in a cosmetic carrier,
(a) at least one anionic direct dye and
(b1) phosphoric acid ($H_3PO_4$) and
(b2) at least one phosphate salt from the group of potassium dihydrogen phosphate ($KH_2PO_4$) and sodium dihydrogen phosphate ($NaH_2PO_4$) and
(c) water,
with the agent that includes the inorganic acid (b1) and the salt or salts of the inorganic acid (b2) in a molar ratio (b1)/(b2) from 1:5 to 5:1.

An agent for coloring keratinic fibers, particularly human hairs, is also very especially preferred which includes, in a cosmetic carrier,
(a) at least one anionic direct dye and
(b1) phosphoric acid ($H_3PO_4$) and
(b2) at least one phosphate salt from the group of potassium dihydrogen phosphate ($KH_2PO_4$) and sodium dihydrogen phosphate ($NaH_2PO_4$) and
(c) water,
with the agent that includes the inorganic acid (b1) and the salt or salts of the inorganic acid (b2) in a molar ratio (b1)/(b2) from 1:3 to 3:1.

An agent for coloring keratinic fibers, particularly human hairs, is also explicitly very especially preferred which includes, in a cosmetic carrier,
(a) at least one anionic direct dye and
(b1) phosphoric acid ($H_3PO_4$) and
(b2) at least one phosphate salt from the group of potassium dihydrogen phosphate ($KH_2PO_4$) and sodium dihydrogen phosphate ($NaH_2PO_4$) and
(c) water,
with the agent that includes the inorganic acid (b1) and the salt or salts of the inorganic acid (b2) in a molar ratio (b1)/(b2) from 1:3 to 1:1.

In other words, an agent for coloring keratinic fibers, particularly human hairs, is explicitly very especially preferred which includes, in a cosmetic carrier,
(a) at least one anionic direct dye and
(b2) an inorganic buffer system comprising (b1) phosphoric acid ($H_3PO_4$) and at least one phosphate salt from the group of potassium dihydrogen phosphate ($KH_2PO_4$) and sodium dihydrogen phosphate ($NaH_2PO_4$) and
(c) water,
with the agent that includes the inorganic acid (b1) and the salt or salts of the inorganic acid (b2) in a molar ratio (b1)/(b2) from 1:3 to 1:1.

As already described above, organic acids and/or the salts of organic acids can tend to result in crystallization to a greater or lesser extent, particularly in colorants with a high solvent content and a pH value set in the acidic range. For example, after the addition of a mixture of citric acid and sodium citrate to the colorants, the formation of crystalline solids contents was observed after several months. This crystallization effect results in unwanted shifts in the pH value and has a disadvantageous impact on the aesthetic appearance of the colorant, and it can also result in inhomogeneities in the resulting color, especially in the area in which the crystals come to rest on the keratinic fiber. For this reason, it is preferred that organic acids not be used to set the pH value and to eliminate the use thereof in the colorant to the greatest possible extent.

In another very especially preferred embodiment, an agent according to the invention is therefore characterized in that (d) the total content of all of the organic carboxylic acids with 1 to 8 C atoms and salts thereof included in the agent—with respect to the total weight of the agent—lies below 0.5 wt %, preferably below 0.5 wt %, more preferably below 0.1 wt %, and very especially preferably below 0.05 wt %.

Organic acids with 1 to 8 C atoms are understood as being any compound that includes at least one C atom and a maximum of 8 C atoms as well as at least one carboxy group (or salt thereof). Therefore, all alkanoic acids (i.e., acetic acid, propionic acid, butanoic acid, etc.) are included by this definition. Moreover, this definition also encompasses all substituted acids, i.e., all compounds which, besides the carboxy group, also possess a hydroxy group and/or an amino group, for example. Food-grade acids such as citric acid, tartaric acid, etc., and aromatic acids such as benzoic acid, for example, also fall under this definition. All salts of the abovementioned acids are likewise covered by this definition, since the salts also tend to produce crystallization.

Example: If an agent includes
(d1) 0.05 wt % citric acid
(d2) 0.1 wt % lactic acid
(d3) 0.05 wt % sodium citrate and
(d4) 0.05 wt % sodium lactate,
then (d) the total content of all organic carboxylic acids with 1 to 8 C atoms and salts thereof included in the agent is 0.25 wt %.

In another very especially preferred embodiment, an agent according to the invention is characterized in that
(d) the total content of all of the acids from the group of citric acid, lactic acid, malic acid, maleic acid, tartaric acid, glycolic acid, succinic acid, fumaric acid, malonic acid, oxalic acid, mandelic acid and the salts of these acids included in the agent—with respect to the total weight of the agent—lies below 0.5 wt %, preferably below 0.3 wt %, more preferably below 0.1 wt %, and very especially preferably below 0.05 wt %.

Citric acid (alternative name: 2-hydroxypropane-1,2,3-tricarboxylic acid) is understood as being the L form of the acid, as well as mixtures thereof.

Lactic acid (alternative names: 2-hydroxypropanoic acid, 2-hydroxypropionic acid) is understood as being the D form of the acid, the L form of the acid, as well as mixtures thereof.

Malic acid (alternative names: hydroxysuccinic acid, hydroxybutanedioic acid) occurs in the R-(+) form and the enantiomeric S-(−) form. Each of these forms and mixtures thereof are in keeping with the invention.

Maleic acid is also alternatively referred to as cis-butenedioic acid and has CAS number 110-16-7. Suitable physiologically acceptable salts of maleic acid are the sodium salt, the potassium salt or the ammonium salt.

Tartaric acid (alternative names: 2,3-dihydroxybutanedioic acid, 2,3-dihydroxysuccinic acid) occurs in 3 stereoisomeric forms: the enantiomers L-(+) tartaric acid and D-(−) tartaric acid, as well as the optically inactive meso form. All of these stereoisomeric forms of tartaric acid and mixtures thereof are in keeping with the invention.

Glycolic acid is also referred to as hydroxyacetic acid and has CAS number 79-14-1.

Succinic acid is alternatively also referred to as butanedioic acid or succinyl acid and has CAS number 110-15-6.

Fumaric acid is the trivial name for trans-butenedioic acid. Fumaric acid has CAS number 110-17-8. Suitable physiologically acceptable salts of fumaric acid are the sodium salt, the potassium salt or the ammonium salt.

Malonic acid is also alternatively referred to as 1,3-propanedioic acid and has CAS number 141-82-2. Suitable physiologically acceptable salts of malonic acid are the disodium salt or the dipotassium salt.

Oxalic acid is alternatively also referred to as ethanedioic acid and has CAS number 144-62-7.

Mandelic acid is alternatively also referred to as hydrophenylacetic acid and has CAS numbers 90-64-2 [(RS)-mandelic acid], 611-71-2 [(R)-mandelic acid] and 17199-29-0 [(S)-mandelic acid]. Mandelic acid occurs in 2 stereoisomers: (R)- and (S)-mandelic acid. All of these stereoisomeric forms of mandelic acid and mixtures thereof are in keeping with the invention.

All of the organic acids cited above are preferably not used in agents according to the invention.

Depending on what type of direct dyes are to be used in the agent according to the invention (neutral, cationic, or anionic), the pH value is preferably set so as to be acidic, neutral or alkaline. It is preferred for the agents according to the invention to be set at an acidic pH value. It is very especially preferred if the agents are set at a pH from 1.0 to 5.5, preferably from 1.8 to 4.9, more preferably from 2.3 to 4.8, and very especially preferably from 2.5 to 3.4.

In another very especially preferred embodiment, an agent according to the invention is therefore characterized in that is has a pH value in the range from 1.0 to 5.5, preferably from 1.8 to 4.9, more preferably from 2.3 to 4.8, and very especially preferably from 2.5 to 3.4.

The pH value can be measured using a glass electrode, for example, which is usually embodied in the form of a single-rod measuring cell. The pH values of the present invention are pH values that are measured at a temperature of 22° C.

The aforedescribed inorganic buffer systems are very especially well-suited for use in formulations which, besides water (c), additionally include at least one solvent or a penetration enhancer. The terms "solvent" and "penetration enhancer" are used synonymously in this context, since all penetration enhancers can generally also act as solvents. Some noteworthy examples of suitable solvents are propylene carbonate, benzyl alcohol, 2-phenoxyethan-1-ol and/or benzyl alcohol.

In another especially preferred embodiment, an agent according to the invention is therefore characterized in that it additionally includes
(e) at least one solvent from the group of propylene carbonate, benzyl alcohol, 2-phenoxyethan-1-ol, and/or benzyl alcohol.

It is very especially advantageous if the colorant according to the invention includes at least one solvent from the group benzyl alcohol, 2-phenoxyethan-1-ol, and/or propylene carbonate. Through the use of one or more solvents from this group, the color uptake of the acid dyes can be enhanced disproportionately. Moreover, it was found that the fastness characteristics of the colorations that can be obtained with the agents according to the invention are better.

Benzyl alcohol is an aromatic alcohol of formula (I); 2-phenoxyethan-1-ol is an aromatic alcohol of formula (II).

(I)

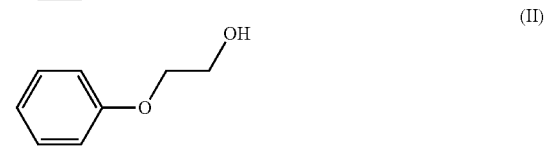

(II)

If keratinic fibers are colored using an agent that includes at least one of the two aromatic alcohols, colorations are obtained with a subsequent coloration with direct acid dyes that are characterized by very good gray coverage effects. The wash fastness of these colorations are also outstanding.

The solvent propylene carbonate also exhibits very good suitability when used in the agent according to the invention.

Propylene carbonate is alternatively also referred to as 4-methyl-1,3-dioxolane-2-on and has the structure of formula (III).

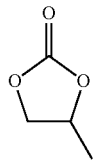

(III)

One very special advantage of the inorganic buffer system (b) is that, when it is used, no crystallization occurs even after an extended period of storage and even in the case of higher solvent quantities in the agent according to the invention.

The agent according to the invention preferably includes the solvents (e) in certain total quantities in the range from 0.5 to 20.0 wt %, preferably from 1.0 to 17.0 wt %, more preferably from 5.0 to 14.0 wt %, and very especially preferably from 8.5 to 12.5 wt %. All indicated quantities are with respect to the total quantity of all of the solvents (e) present in the agent correlated with the total weight of the agent.

In another very especially preferred embodiment, an agent according to the invention is therefore characterized in that it includes—with respect to the total weight of the agent—one or more solvents in a total quantity from 0.5 to 20.0 wt %, preferably from 1.0 to 17.0 wt %, more preferably from 5.0 to 14.0 wt %, and very especially preferably from 8.5 to 12.5 wt %.

Through the use of the inorganic buffer system according to the invention (b), the desired pH value can be set at the desired value in a reliable and long-lasting manner. Even fluctuations in the quality and in the specifications of the other ingredients additionally used in the colorant do not negatively impact the pH value.

Another special advantage of the inorganic buffer system (b) is that, in this way, the hardness of the water used to produce the agent can no longer have an erratic effect. For reasons of cost, distilled water is generally not used for the production of colorants, but rather common municipal water from the production site. Depending on the hardness of the water of the respective region, the water can therefore include different quantities of dissolved salts that can have an influence on the pH value of the agent. Through the use of the inorganic buffer system (b) according to the invention, this influence can be eliminated.

Water hardness refers to the equivalent concentration of the ions of the alkaline earth metals dissolved in the water. The hardness constituents basically include calcium and magnesium ions, as well as strontium and barium ions, which are normally included only in trace amounts. The dissolved hardness constituents can form insoluble compounds, especially limescale and lime soaps. Hard water occurs particularly in regions in which sandstones and limestones are predominant.

The total hardness of the water is indicated by the sum of the concentrations of the cations of alkaline earth metals in water. The majority of water hardness—and the part that is most important with regard to the influencing of the pH value—occurs as a result of the dissolution of calcium carbonate ($CaCO_3$) and/or dolomite (Ca—Mg mixed carbonate) through carbonic acid under formation of soluble hydrogen carbonates ($HCO_3^-$).

With respect to water hardness, the concentration of the anion hydrogen carbonate ($HCO_3^-$) is of special importance. The concentration of hydrogen carbonate ions and the portion of the alkaline earth metal ions equivalent thereto are referred to as the carbonate, temporary, or transient hardness.

The best known practicable method for determining total hardness is complexometric titration with an aqueous solution of the disodium salt of ethylenediaminetetraacetic acid (EDTA, trade name: Titriplex III) having a known concentration. With the hardness constituents $Ca^{2+}$ and $Mg^{2+}$, EDTA forms soluble, stable chelate complexes. 100 ml of the water sample to be tested are mixed, for example, with 2 ml of 25% ammoniac solution, a pH 11 buffer (ammoniac-ammonium acetate), and the indicator Eriochrome Black T. Usually, the indicator can be obtained together with the buffer as so-called "indicator-buffer tablets." When masked with a yellow dye, the indicator forms a red-colored complex with the $Ca^{2+}$ and $Mg^{2+}$. If these ions are bound by the EDTA at the end of titration, the Eriochrome Black T is present in free form and is green-colored. In the case of an unmasked indicator, the color change is from magenta to blue. The total hardness is calculated from the volume of EDTA solution consumed. In the case of a 100 ml water sample, 1 ml of consumed EDTA solution (c=0.1 mol/l) corresponds to 5.6° dH (German degrees of hardness), which corresponds to 1 mmol/l alkaline earth ions. In order to identify the calcium and magnesium concentration individually, in the case of a lower pH of about 8, titration is first performed of $Ca^{2+}$ with EDTA, because the Mg-EDTA complex is not yet stable at that pH. At the point of change of calcium, the pH is then set at 11, and titration of $Mg^{2+}$ is performed with EDTA.

According to the SI system of units, the content of alkaline earth ions, that is, the total hardness is indicated in mols per liter, or, in the case of small concentrations, in millilols per liter (mmol/l). In Germany, the water hardness is usually indicated in Germany in German degrees of hardness (° dH), which can be calculated according to the following formula (unit mg/l):

$$° dH=0.14\times[\text{Ca value in mg/l}]+0.23\times[\text{Mg value in mg/l}]$$

| Hardness scale | °dH |
| --- | --- |
| 1 (soft water) | to 7.3 |
| 2 (medium water hardness) | 7.3 to 14 |
| 3 (hard water) | 14 to 21.3 |
| 4 (very hard water) | over 21.3 |

In another very especially preferred embodiment, an agent according to the invention is therefore characterized in that it (c) includes water with a degree of hardness (° dH) of at least 7.3, preferably of at least 9.3, more preferably of at least 11.3, and especially preferably of at least 14.3, with the degree of hardness being calculated according to the following formula (mg calcium and magnesium per liter of water):

$$° dH=0.14\times[\text{Ca value in mg/l}]+0.23\times[\text{Mg value in mg/l}]$$

The agent according to the invention can be packaged in various forms. For example, it can be applied as a gel, as an emulsion, as a solution, or even in the form of a coloring foam. The use of coloring foams represents an especially attractive and comfortable form of application for the user. In order to obtain a coloring foam, the agent can be packaged in the form of an aerosol, for example. The aerosol packaging type requires the use of a spray head with valve and is therefore especially sensitive to the formation of crystals.

An aerosol is a disperse system in which a solid or a liquid is present in a very finely distributed gas. The aerosol is generally produced only at the time of application with the aid of a suitable spraying system through the spraying of solutions, emulsions, or suspensions, for which purpose spray cans can be used, for example, in which a liquefied pressurized has serves as a propellant gas. When the pressure valve is opened, the propellant preparation mixture escapes through a fine nozzle that volatilizes the propellant and leaves behind the finely distributed spray product as an aerosol or spray foam.

As already described above, crystallization can occur over time in buffer systems that are based on the use of food-grade acids such as citric acid, for example, and their corresponding bases. If citric acid or a citrate salt then crystallizes in the colorant located in the pressurized aerosol container, then the valve can be clogged when the colorant passes through the spray head, thus preventing further use of the colorant.

Through the use of the buffer system (b) according to the invention in the colorant, crystallization is prevented, thereby also enabling the packaging of the colorant as a spray foam in the form of an aerosol.

When packaged in the form of an aerosol, the agent according to the invention further comprises at least one propellant gas. Some examples of suitable propellant gases that can be used are dimethyl ether, propane, propene, n-butane, iso-butane, iso-butene, n-pentane, pentene, iso-pentane and/or iso-pentene.

In another especially preferred embodiment, an agent according to the invention is therefore characterized in that it additionally includes
(f) one or more other propellant gases selected from the group of dimethyl ether, propane, propene, n-butane, iso-butane, iso-butene, n-pentane, pentene, iso-pentane and iso-pentene.

Furthermore, it has been found to be preferable if the propellant gases (f) are also included in certain quantity ranges in the composition. In a preferred embodiment, the agent therefore includes—with respect to the total weight of the propellant-containing composition—one or more additional propellant gases (f) in a total quantity from 1 to 10 wt %, preferably from 2 to 9 wt %, more preferably from 3 to 8 wt %, and especially preferably from 4 to 7 wt %.

The agents according to the invention further comprise additional active substances, adjuvants, and additives in order to improve the coloring performance and set additional desired characteristics of the agents.

Preferably, the agents are prepared as a liquid preparation and another, surface-active substance is therefore optionally added to the agents, with such surface-active substances being referred to as surfactants or as emulsifiers, depending on the area of application: They are preferably selected from among anionic, zwitterionic, amphoteric and nonionic surfactants and emulsifiers.

Agents that are suitable according to the invention are characterized in that the agent additionally includes at least one anionic surfactant. Preferred anionic surfactants are fatty acids, alkyl sulfates, alkyl ether sulfates, and ether carboxylic acids with 10 to 20 C atoms in the alkyl group and up to 16 glycol ether groups in the molecule. The anionic surfactants are used in proportions of 1.0 to 45 wt %, preferably 1 to 30 wt % and very especially preferably 1 to 15 wt % with respect to the total quantity of the agent.

Agents that are suitable according to the invention are characterized in that the agent additionally includes at least one zwitterionic surfactant. Preferred zwitterionic surfactants are betaines, N-alkyl-N,N-dimethylammonium glycinates, N-acyl-aminopropyl-N,N-dimethylammonium glycinates, and 2-alkyl-3-carboxymethyl-3-hydroxyethyl-imidazolines. One preferred zwitterionic surfactant is known under the INCI designation as cocoamidopropyl betaine.

Agents that are suitable according to the invention are characterized in that the agent additionally includes at least one amphoteric surfactant. Preferred amphoteric surfactants are N-alkyl-glycines, N-alkylaminopropionic acids, N-alkylaminobutyric acids, N-alkyliminodipropionic acids, N-hydroxy-ethyl-N-alkylamidopropyl glycines, N-alkyl taurines, N-alkyl sarcosines, 2-alkylaminopropionic acids and alkylamino acetic acids. Especially preferred amphoteric surfactants are N-cocoalkyl-amino propionate, as cocoacylamino-ethylaminopropionate and $C_{12}$-$C_{18}$ acyl sarcosine.

Moreover, it has proven advantageous if the agents include other, non-ionogenic boundary surface-active substances. Preferred nonionic surfactants are alkyl polyglycosides as well as alkylene oxide addition products to fatty alcohols, and fatty acids, each with 2 to 30 mols of ethylene oxide per mol of fatty alcohol or fatty acid. Preparations with outstanding characteristics are also obtained if they include fatty acid esters of ethoxylated glycerin as nonionic surfactants.

The nonionic, zwitterionic or amphoteric surfactants are used in proportions of 1.0 to 45 wt %, preferably 1 to 30 wt % and very especially preferably 1 to 15 wt % with respect to the total quantity of the agent.

It has also proven advantageous if the agents include at least one thickener. In principle, no restrictions exist with respect to these thickeners. Both organic and purely inorganic thickeners can be used.

Suitable thickeners are anionic, synthetic polymers; cationic, synthetic polymers; naturally occurring thickeners such as nonionic guar gums, scleroglucan gums or xanthan gums, gum arabic, ghatti gum, karaya gum, tragacanth gum, carrageenan gum, agar-agar, locust bean gum, pectins, alginates, starch fractions and derivatives such as amylose, amylopectin and dextrins, as well as cellulose derivatives such as methyl cellulose, carboxyalkyl celluloses and hydroxyalkyl celluloses; nonionic, fully synthetic polymers such as polyvinyl alcohol or polyvinyl pyrrolidone; as well as inorganic thickeners, particularly layered silicates such as bentonite, especially smectites such as montmorillonite or hectorite.

The agent according to the invention can also include anionic polymeric thickeners. Suitable compounds are selected, for example, from the crosslinked or non-crosslinked copolymers which include at least two different monomers from the group of acrylic acid, methacrylic acid, the $C_1$-$C_6$ alkyl esters of acrylic acid, and/or the $C_1$-$C_6$ alkyl esters of methacrylic acid. Especially preferred anionic copolymers are copolymers of acrylic acid, methacrylic acid, or the $C_1$-$C_6$ alkyl esters thereof, which are sold under the INCI designation Acrylates Copolymer. The combination of methacrylic acid and ethyl acrylate, as well as optionally crosslinking, multifunctional monomers, is particularly preferred. One example of a preferred commercial product for this is Aculyn® 33 or 33A, which is offered by Rohm & Haas.

Furthermore, the agent according to the invention can include one or more polymers from the group of polyquaternium-1, polyquaternium-2, polyquaternium-3, polyquaternium-4, polyquaternium-5, polyquaternium-6, polyquaternium-7, polyquaternium-8, polyquaternium-9, polyquaternium-10, polyquaternium-11, polyquaternium-14, polyquaternium-16, polyquaternium-17, polyquaternium-18, polyquaternium-22, polyquaternium-24, polyquaternium-27, polyquaternium-28, polyquaternium-32, polyquaternium-33, polyquaternium-37, polyquaternium-39, polyquaternium-44, polyquaternium-46, polyquaternium-53, polyquaternium-55, polyquaternium-64, polyquaternium-67, polyquaternium-68, polyquaternium-69 and/or polyquaternium-86.

In one embodiment, the agents according to the invention can also include one or more cationic surfactants. According to the invention, all common cationic surfactants known to a person skilled in the art can be used as cationic surfactants. These include:

quaternary imidazoline compounds. Formula Quimi I shown below shows the structure of these compounds.

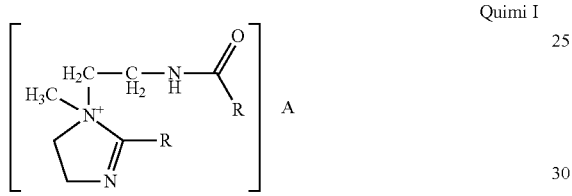

(Quimi I)

The residues R, independently of one another, each stand for a saturated or unsaturated, linear or branched hydrocarbon residue with a chain length of 8 to 30 carbon atoms. The preferred compounds of formula I include the same hydrocarbon residue for R in each case. The chain length of the residues R is preferably 12 to 21 carbon atoms. Exemplars that are especially preferred according to the invention can be obtained under the INCII designations quaternium-27, quaternium-72, quaternium-83 and quaternium-91.

Cationic surfactants according to formula (Tkat-2),

RCO—X—$N^+R^1R^2R^3$ $A^-$ (Tkat-2)

R stands herein for a substituted or unsubstituted, branched or linear alkyl or alkenyl residue with 11 to 35 carbon atoms in the chain, X stands for —O— or —$NR^5$—, $R^1$ stands for an alkylene group with 2 to 6 C atoms, which can be substituted or unsubstituted, with substitution with an —OH— or —NH— group being preferred in the case of a substitution, $R^2$, $R^3$, each independently of one another, stand for an alkyl or hydroxyalkyl group with 1 to 6 C atoms in the chain, with the chain being linear or branched.

R5 stands for hydrogen or a C1 to C6 straight-chain or branched alkyl or alkenyl residue, which can also be substituted by a hydroxy group.

Within this structural class, the compounds of one of the following structures are preferably used:

$CH_3(CH_2)_{20}CONH(CH_2)_3$—$N^+(CH_3)_2$—$CH_2CH_3$ $A^-$ (Tkat-3)

$CH_3(CH_2)_{20}CONH(CH_2)_3$—$N^+(CH_3)_2$—$CH_2$(CHOH)$CH_2OH$ $A^-$ (Tkat-4)

$CH_3(CH_2)_{20}COOCH_2CHOHCH_2$—$N^+(CH_3)_3$ $A^-$ (Tkat-5)

$CH_3(CH_2)_{20}CONH(CH_2)_3$—$N^+(CH_3)_2$—$CH_2CH_2OH$ $A^-$ (Tkat-6)

Examples of such commercial products are Schercoquat BAS, Lexquat AMG-BEO, Akypoquat 131 or Incroquat Behenyl HE.

Esterquats according to formula (Tkat1-2) be used.

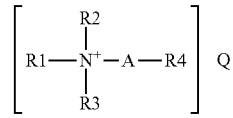

(Tkat1-2)

Herein, the residues R1, R2, and R3 are each independent of one another and can be the same or different. The residues R1, R2, and R3 refer to:
a branched or unbranched alkyl group with 1 to 4 carbon atoms that can include at least one hydroxyl group, or
a saturated or unsaturated, branched or unbranched, or a cyclic saturated or unsaturated alkyl group with 6 to 30 carbon atoms that can include at least one hydroxyl group, or
an aryl or alkaryl residue, for example phenyl or benzyl,
the residue (-A-R4), on the condition that no more than 2 of the residues R1, R2, or R3 can stand for this residue:
The residue -(A-R4) is included at least 1 to 3 times.
Herein, A stands for:
1) —(CH2)n-, where n=1 to 20, preferably n=1 to 10 and especially preferably n=1-5, or
2) —(CH2-CHR5-O)n-, where n=1 to 200, preferably 1 to 100, especially preferably 1 to 50, and more especially preferably 1 to 20, where R5 refers to hydrogen, methyl, or ethyl, and
R4 stands for:
1) R6-O—CO—, where R6 is a saturated or unsaturated, branched or unbranched, or a cyclic saturated or unsaturated alkyl residue with 6 to 30 carbon atoms that can include at least one hydroxy group and that can optionally also be oxethylated with 1 to 100 ethylene oxide units and/or 1 to 100 propylene oxide units, or
2) R7-CO—, where R7 is a saturated or unsaturated, branched or unbranched or a cyclic saturated or unsaturated alkyl residue with 6 to 30 carbon atoms that can include at least one hydroxy group and that can optionally also be oxethylated with 1 to 100 ethylene oxide units and/or 1 to 100 propylene oxide units, and
Q stands for a physiologically acceptable organic or inorganic anion.
Such products are sold, for example, under the trademarks Rewoquat®, Stepantex®, Dehyquart®, and Armocare®. The products Armocare® VGH-70, an N,N-bis(2-palmitoyloxyethyl)dimethylammonium chloride, as well as Dehyquart® F-75, Dehyquart® C-4046, Dehyquart® L80, Dehyquart® F-30, Dehyquart® AU-35, Rewoquat® WE18, Rewoquat® WE38 DPG, and Stepantex® VS 90 are examples of such esterquats.
Other compounds of the formula (Tkat1-2) that are especially preferred according to the invention belong to the formula (Tkat1-2.1), the cationic betaine esters.

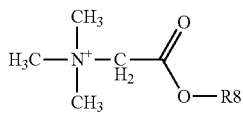
(Tkat1-2.1)

R8 corresponds in its meaning to R7.

Monoalkyltrimethylammonium salts with a chain length of the alkyl residue of 16 to 24 carbon atoms corresponding to formula (Tkat1-1),

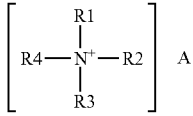
(Tkat1-1)

in which R1, R2, and R3 each stand for a methyl group and R4 for a saturated, branched or unbranched alkyl residue with a chain length of 14 to 24 carbon atoms. Examples of compounds of formula (Tkat1-1) are cetyltrimethylammonium chloride, cetyltrimethylammonium bromide, cetyltrimethylammonium methosulfate, stearyltrimethylammonium chloride, behenyltrimethylammonium chloride, behenyltrimethylammonium bromide, and behenyltrimethylammonium methosulfate.

Amines and/or cationized amines, particularly an amidoamine and/or a cationized amidoamine, with the following structural formulas:

(Tkat7)

and/or

(Tkat8)

where R1 refers to an acyl or alkyl residue with 6 to 30 C atoms that can be branched or unbranched, saturated or unsaturated, and where the acyl residue and/or the alkyl residue can include at least one OH group, and R2, R3, and R4, each independently of one another, can be hydrogen or an alkyl residue with 1 to 4 C atoms that can be the same or different, saturated or unsaturated, and $X^-$ refers to an anion and n refers to an integer between 1 and 10.

A composition is preferred in which the amine and/or the quaternized amine according to general formulas (Tkat7) and/or (Tkat8) is an amidoamine and/or a quaternized amidoamine, where R1 is a branched or unbranched, saturated or unsaturated acyl residue with 6 to 30 C atoms that can include at least one OH group. A fatty acid residue from oils and waxes, preferably from natural oils and waxes, is preferred here. Examples that merit consideration for this are lanolin, beeswaxes, or candelilla waxes. Such amidoamines and/or quaternized amidoamines are also preferred in which, in formulas (Tkat7) and/or (Tkat8), R2, R3, and/or R4 refer to a residue according to the general formula $CH_2CH_2OR5$, where R5 can refer to alkyl residues with 1 to 4 carbon atoms, hydroxyethyl or hydrogen. The preferred value of n in the general formulas (Tkat7) and/or (Tkat8) is an integer between 2 and 5. Also preferred are amidoamines and/or quaternized amidoamines of the general formulas (Tkat7) and/or (Tkat8), in which the anion $X^-$ is a halide ion or a compound of the general formula $RSO_3^-$, where R has the meaning of saturated or unsaturated alkyl residues with 1 to 4 carbon atoms. The alkyl residue with 1 to 4 carbon atoms of R2, R3 and R4 and/or the alkyl residue with 1 to 4 carbon atoms of $RSO_3^-$ in the general formula (Tkat7) and/or (Tkat8) can include at least one hydroxyl group. The alkyl amidoamines can be present both as such and be converted by protonation in commensurately acidic solution into a quaternary compound in the composition. The cationic alkyl amidoamines are preferred according to the invention.

The following amidoamines to be used according to the invention what can be quaternized merit consideration as amidoamines: Witcamine® 100 (Witco, INCI designation: Cocamidopropyl Dimethylamine), Incromine® BB (Croda, INCI designation: Behenamidopropyl Dimethylamine), Mackine® 401 (McIntyre, INCI designation: Isostearylamidopropyl Dimethylamine) and other Mackine types, Adogen® S 18V (Witco, INCI designation: Stearylamidopropyl Dimethylamine), and, as permanently cationic amidoamines: Rewoquat® RTM 50 (Witco Surfactants GmbH, INCI designation: Ricinoleamidopropyltrimonium Methosulfate), Empigen® CSC (Albright&Wilson, INCI designation: Cocamidopropyltrimonium Chloride), Swanol® Lanoquat DES-50 (Nikko, INCI designation: Quatemium-33), Rewoquat® UTM 50 (Witco Surfactants GmbH, Undecyleneamidopropyltrimonium Methosulfate).

The anion of all of the previously described cationic compounds is selected from among the physiologically acceptable anions. Examples of these are the halide ions, fluoride, chloride, bromide, sulfate of the general formula $RSO_3^-$, where R has the meaning of saturated or unsaturated alkyl residues with 1 to 4 carbon atoms, or anionic residues of organic acids such as maleate, fumarate, oxalate, tartrate, citrate, lactate, or acetate.

Cationic imidazolines, esterquats, cationic surfactants according to formula (Tkat-2) as well as amines and/or cationized amines, particularly amidoamines and/or cationized amidoamines are preferably used.

The aforementioned cationic surfactants can be used individually or in any combination with one another, with quantities between 0.01 and 20 wt %, preferably quantities from 0.01 to 10 wt %, and very especially preferably quantities from 0.1 to 7.5 wt % included. The very best results are obtained with quantities from 0.1 to 5 wt %, each with respect to the overall composition of the respective agent.

The surfactants are used in a total quantity of the surfactants in quantities of 0.05 to 45 wt %, preferably 0.1 to 30 wt %, and very especially preferably 0.5 to 25 wt %, with respect to the total agent used according to the invention.

The cationic surfactants are used in proportions of 0.1 to 45 wt %, preferably 1 to 30 wt %, and very especially preferably 1 to 15 wt %—each with respect to the total quantity of the agent.

Furthermore, the agents according to the invention can include other active substances, adjuvants and additives, such as, for example, nonionic polymers such as, for example, vinylpyrrolidone/vinyl acrylate copolymers, polyvinylpyrrolidone, vinylpyrrolidone/vinyl acetate copolymers, polyethylene glycols and polysiloxanes; additional silicones such as volatile or nonvolatile, straight-chain, branched or cyclic, crosslinked or non-crosslinked polyalkylsiloxanes (such as dimethicone or cyclomethicone), polyarylsiloxanes and/or polyalkylarylsiloxanes, particularly polysiloxane with organofunctional groups, such as substituted or unsubstituted amines (amodimethicone), carboxyl, Alkoxy and/or hydroxyl groups (dimethicone copolyols), linear polysiloxaneA)-polyoxyalkyleneB) block copolymers, grafted silicon polymers; cationic polymers such as quaternized cellulose ethers, polysiloxanes with quaternary groups, dimethyldiallyl ammonium chloride polymers, acrylamide dimethyldiallyl ammonium chloride copolymers, dimethylamino-ethylmethacrylate vinylpyrrolidone copolymers quaternized with diethyl sulfate, vinylpyrrolidone imidazolinium methochloride copolymers and quaternized polyvinyl alcohol; zwitterionic and amphoteric polymers; anionic polymers such as, for example, polyacrylic acids or crosslinked polyacrylic acids; lipids such as, for example, $C_8$-$C_{30}$ fatty alcohols, hydrocarbons, or natural oils and fats; structurants such as glucose, maleic acid and lactic acid, hair-conditioning compounds such as phospholipids, for example lecithin and cephaline; perfume oils, dimethyl isosorbide and cyclodextrins; fiber structure-improving active substances, particularly mono-, di- and oligosaccharides such as, for example, glucose, galactose, fructose, fruit sugar and lactose; colorants for coloring the agent; anti-dandruff agents such as piroctone olamine, zinc omadine and climbazol; amino acids and oligopeptides; animal- and/or plant-based protein hydrolysates, as well as in the form of their fatty acid condensation products or, optionally, anionically or cationically modified derivatives; plant oils; light stabilizers and UV blockers; active substances such as panthenol, pantothenic acid, pantolactone, allantoin, pyrrolidone carboxylic acids and salts thereof, as well as bisabolol; polyphenoles, particularly hydroxycinnamic acids, 6,7-dihydroxycoumarins, hydroxybenzoic acids, catechins, tannins, leucoanthocyanidins, anthocyanidins, flavanones, flavones, and flavonols; ceramides or pseudo-ceramides; vitamins, provitamins and vitamin precursors; plant extracts; fats and waxes such as fatty alcohols, beeswax, montan wax and paraffins; swelling and penetration agents such as glycerin, propylene glycol monoethyl ethers, carbonates, hydrogen carbonates, guanidine, ureas as well as primary, secondary and tertiary phosphates; opacifiers such as latex, styrene/PVP and styrene/acrylamide copolymers; pearlescent agents such as ethylene glycol mono- and distearate as well as PEG-3 distearate and pigments.

The selection of these other substances is made by a person skilled in the art depending on the desired characteristics of the agents. As regards other optional components as well as the quantities of these components used, express reference is made to the relevant handbooks known to a person skilled in the art. The additional active substances and adjuvants are preferably each used in the agents according to the invention in quantities from 0.0001 to 25 wt %, particularly from 0.0005 to 15 wt %, with respect to the total weight of the respective agent.

The packaging of the agent in the form of an aerosol is explicitly very especially preferred.

A second object of the present invention is therefore a cosmetic product comprising a cosmetic agent of the first object of the invention which is packaged in a pressurized aerosol container, with the pressurized aerosol container possessing an aerosol dispensing device with spray valve.

The cosmetic product of the second object of the invention comprises a pressurized aerosol container. Vessels that merit consideration as pressurized gas containers are those made of metal (aluminum, tinplate, tin), protected or non-splitting plastic, or glass that is coated with plastic on the outside, with compressive and breaking strength, corrosion resistance, ease of fillability as well as aesthetic aspects, manageability, printability, etc., playing a role in the selection thereof. Special interior protective coatings ensure corrosion resistance in relation to the preparation included in the pressurized aerosol container.

It is especially advantageous if the internal pressure of the pressurized aerosol container is at least 1.8 bar, particularly at least 2.5 bar.

The product further comprises an aerosol dispensing device possessing a spray valve for dispensing the aerosol. In a preferred embodiment of the invention, the spray valve has a valve plate coated with a paint or a polymeric plastic A and such a flexible element with return characteristic that returns the valve to the closed position (=idle position of the valve) upon completion of actuation. Corresponding cosmetic products in which the aerosol dispensing device comprises a valve having a valve cone and/or a flexible element with return characteristic that is/are coated with a paint or a polymeric plastic A are preferred according to the invention.

In another preferred embodiment of the invention, the spray valve has a flexible element with return characteristic and/or a valve plate made of at least one plastic B, preferably an elastomeric plastic. Here as well, cosmetic products according to the invention in which the valve has a flexible element with return characteristic and/or a valve cone made of at least one plastic B, with preferred plastics B being elastomeric plastics. Especially preferred elastomeric plastics are selected from Buna, particularly Buna N, Buna 421, Buna 1602 and Buna KA 6712, neoprene, butyl and chlorobutyl.

In another preferred embodiment of the invention, the flexible element with return characteristic can be embodied as a spiral spring or helical compression spring. In another preferred embodiment of the invention, the flexible element of the valve with return characteristic can be integrally formed with the valve cone and have flexible legs. This spring can be made of metal or plastic.

In an especially preferred embodiment of the invention, valve cone and flexible element are embodied so as to have return characteristics. The valve type Ariane M, available from Seaquist Perfect, in which the flexible element with return characteristic is integrally formed with the valve cone in the form of four elastic legs is especially preferred.

All spray valves used according to the invention preferably have a valve plate with an interior coating, with coating and valve material being compatible with one another. If aluminum valves are used according to the invention, their valve plates can be coated with a Micoflex coating, for example. If tinplate valves are used according to the invention, their valve plates can be coated with PET (polyethylene terephthalate), for example. The containers used, which can be made of tinplate or aluminum, for example, with aluminum containers being preferred according to the invention, must also be varnished or coated on the inside in view of the corrosiveness of the water-in-oil emulsions used according to the invention. In interior protective coating that is preferred according to the invention is an epoxy phenol varnish such as that available under the name Hoba 7407 P.

Very especially preferably, the valve is a valve of the type Aptar ARM-4.00-1-0, 32-8, 70 Green—AR Housing—Valve-AHT-1.60-0.00-PA-Natural.

As regards other preferred embodiments of the cosmetic product according to the invention, the remarks concerning the agents according to the invention apply mutatis mutandis.

Through the addition of an inorganic buffer system (b) to the colorants, which include at least one (a) direct dye and (c) water, the pH value of the agents can be set in a precise and reproducible manner. This means that even the color and color nuances that are achieved through the use of the colorant on the hair become better reproducible and optimized with regard to their nuance stability.

A third object of the present invention is therefore a method for increasing the nuance stability of colorants, characterized in that an agent for coloring keratinic fibers which includes
(a) at least one direct dye, and
(c) water, is mixed with
(b) an inorganic buffer system consisting of at least one inorganic acid (b1) and at least one inorganic salt of this acid or these acids (b2), as was disclosed in detail in the description of the first object of the invention.

As regards other preferred embodiments of the cosmetic method according to the invention, the remarks concerning the agents and products according to the invention apply mutatis mutandis.

EXAMPLES

The following pre-solutions (PRE) were prepared: The pH value of the pre-solution was then measured:
1. Measurement of Changes in the pH Value

| Dye-containing preparation (F) | (F) |
|---|---|
| Coco glucoside (nonionic surfactant) | 1.5 g |
| Phenoxyethanol (solvent) | 0.81 g |
| Xanthan (thickener) | 1.0 g |
| Benzyl alcohol (solvent) | 9.4 g |
| Acid Black No. 1 (acid dye) | 0.4 g |
| Acid Violet 43 (acid dye) | 0.3 g |
| Food Yellow 13 (acid dye) | 0.1 g |
| Acid Red 52 (acid dye) | 0.5 g |
| Perfume | 0.5 g |
| Water (°dH = 14.3-14.4) | Up to 20 g |

Once the mixture of (PRE) and (F) was obtained, the pH value of each resulting mixture was measured again. The smaller the difference in the pH values between (PRE) and [(PRE)+(F)] is, the greater the buffer capacity of the buffer used (b1)+(b2).

|  | (PRE1) | (PRE2) | (PRE3) |
|---|---|---|---|
| Phosphoric acid ($H_3PO_4$) (b1) | 0.26 g | 0.77 g | 1.36 g |
| Molar mass = 97.95 g/mol | (2.7 mmol) | (7.9 mmol) | (13.9 mmol) |
| Potassium dihydrogen phosphate ($KH_2PO_4$) (b2) | 3.0 g | 3.0 g | 3.0 g |
|  | (22.1 mmol) | (22.1 mmol) | (22.1 mmol) |
| Molar mass = 136.032 g/mol |  |  |  |
| Molar ratio (b1)/(b2) | 1:8.3 | 1:2.8 | 1:1.6 |
| Water (°dH = 14.3-14.4) | up to 80 g | up to 80 g | up to 80 g |
| pH of the pre-solution | 3.06 | 2.43 | 2.03 |
|  | (PRE4) | (PRE5) | (PRE6) |
| Phosphoric acid ($H_3PO_4$) (b1) | 0.59 g | 0.43 g | 0.94 g |
| Molar mass = 97.95 g/mol | (6.0 mmol) | (4.4 mmol) | (9.6 mmol) |
| Potassium dihydrogen phosphate ($KH_2PO_4$) (b2) | 3.0 g | 3.0 g | 3.0 g |
|  | (22 mmol) | (22 mmol) | (22 mmol) |
| Molar mass = 136.032 g/mol |  |  |  |
| Molar ratio (b1)/(b2) | 1:3.7 | 1:5.0 | 1:2.3 |
| Water | Up to 80 g | Up to 80 g | Up to 80 g |
| pH of the pre-solution | 2.90 | 2.87 | 2.42 |

After that, each of the abovementioned pre-solutions was mixed with the following dye-containing preparation (F)

|  | (PRE1) | (PRE2) | (PRE3) |
|---|---|---|---|
| Phosphoric acid ($H_3PO_4$) (b1) | 0.26 g | 0.77 g | 1.36 g |
| Molar mass = 97.95 g/mol | (2.7 mmol) | (7.8 mmol) | (13.9 mmol) |
| Potassium dihydrogen phosphate ($KH_2PO_4$) (b2) | 3.0 g | 3.0 g | 3.0 g |
|  | (22.1 mmol) | (22.1 mmol) | (22.1 mmol) |
| Molar mass = 136.032 g/mol |  |  |  |
| Molar ratio (b1)/(b2) | 1:8.3 | 1:2.8 | 1:1.6 |
| pH of the pre-solution (P) | 3.06 | 2.43 | 2.03 |
| pH of the mixture (P) + (F) | 3.36 | 2.67 | 2.20 |
| Change in pH value | 0.3 | 0.24 | 0.17 |
|  | (PRE4) | (PRE5) | (PRE6) |
| Phosphoric acid ($H_3PO_4$) (b1) | 0.59 g | 0.43 g | 0.94 g |
| Molar mass = 97.95 g/mol | (6.0 mmol) | (4.4 mmol) | (9.6 mmol) |
| Potassium dihydrogen phosphate ($KH_2PO_4$) (b2) | 3.0 g | 3.0 g | 3.0 g |
|  | (22 mmol) | (22 mmol) | (22 mmol) |
| Molar mass = 136.032 g/mol |  |  |  |
| Molar ratio (b1)/(b2) | 1:3.7 | 1:5.0 | 1:2.3 |
| pH of the pre-solution | 2.90 | 2.87 | 2.42 |
| pH of the mixture (P) + (F) | 3.05 | 3.16 | 2.58 |
| Change in pH value | 0.15 | 0.29 | 0.16 |

2. Measurement of Storage Stability

The following preparations were prepared and stored in glass containers with screw lid for 3 months at room temperature. The glass containers were inspected visually immediately after preparation and after 3 months.

| | Colorant | |
|---|---|---|
| | (P) | (E) |
| Phosphoric acid (H$_3$PO$_4$) | — | Up to pH 2.5 |
| Sodium dihydrogen phosphate (NaH$_2$PO$_4$) | — | 2.0 g |
| Citric acid | Up to pH 2.5 | — |
| Sodium citrate | 2.0 g | — |
| Coco glucoside (nonionic surfactant) | 1.5 g | 1.5 g |
| Phenoxyethanol (solvent) | 0.81 g | 0.81 g |
| Xanthan (thickener) | 1.0 g | 1.0 g |
| Benzyl alcohol (solvent) | 9.4 g | 9.4 g |
| Acid Black No. 1 (acid dye) | 0.4 g | 0.4 g |
| Acid Violet 43 (acid dye) | 0.3 g | 0.3 g |
| Food Yellow 13 (acid dye) | 0.1 g | 0.1 g |
| Acid Red 52 (acid dye) | 0.5 g | 0.5 g |
| Perfume | 0.5 g | 0.5 g |
| Water (°dH = 14.3-14.4) | Up to 100 g | Up to 100 g |
| Immediately after preparation | Colored gel without solids | Colored gel without solids |
| After 3 months of storage | Solids contents visible | Colored gel without solids |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. An agent for coloring keratinic fibers, particularly human hairs, including in a cosmetic carrier
   (a) at least one direct dye,
   (b) an inorganic buffer system comprising at least one inorganic acid (b1) and at least one inorganic salt of this acid or these acids (b2), and
   (c) water, and wherein;
   the agent is free of organic carboxylic acids with 1 to 8 carbon atoms, such that a total of all organic carboxylic acids with 1 to 8 carbon atoms in the agent is less than 0.5 weight percent, with respect to a total weight of the agent.

2. The agent as set forth in claim 1, wherein the at least one direct dye (a) includes at least one anionic direct dye.

3. The agent as set forth in claim 1, wherein the at least one direct dye (a) includes at least one selected from the group consisting of Acid Yellow 1, Acid Yellow 3, Acid Yellow 9, Acid Yellow 17, Acid Yellow 23, Acid Yellow 36, Acid Yellow 121, Acid Orange 6, Acid Orange 7, Acid Orange 10, Acid Orange 11, Acid Orange 15, Acid Orange 20, Acid Orange 24, Acid Red 14, Acid Red 18, Acid Red 27, Acid Red 33, Acid Red 35, Acid Red 51, Acid Red 52, Acid Red 73, Acid Red 87, Acid Red 95, Acid Red 184, Acid Red 195, Acid Violet 43, Acid Violet 49, Acid Violet 50, Acid Blue 1, Acid Blue 3, Acid Blue 7, Acid Blue 104, Acid Blue 9, Acid Blue 62, Acid Blue 74, Acid Blue 80, Acid Green 3, Acid Green 5, Acid Green 9, Acid Green 22, Acid Green 25, Acid Green 50, Acid Black 1, Acid Black 52, Food Yellow 8, Food Blue 5, D&C Yellow 7, D&C Yellow 8, D&C Orange 4, D&C Green 5, D&C Orange 10, D&C Orange 11, D&C Red 21, D&C Red 27, D&C Red 33, D&C Violet 2 and D&C Brown 1.

4. The agent as set forth in claim 1, wherein the inorganic acid (b1) and the salt or salts of the inorganic acid (b2) are included in a molar ratio (b1)/(b2) of from 1:15 to 15:1.

5. The agent as set forth in claim 1, wherein the agent includes—with respect to the total weight of the agent—(b1) one or more inorganic acids in a total quantity from 0.1 to 5.0 wt %.

6. The agent as set forth in claim 1, wherein the agent includes—with respect to the total weight of the agent—(b2) one or more salts of the inorganic acid(s) in a total quantity from 0.1 to 5.0 wt %.

7. The agent as set forth in claim 1, wherein the inorganic buffer system (b) consists of
   (b1) phosphoric acid (H$_3$PO$_4$) and
   (b2) at least one phosphate salt selected from the group consisting of potassium dihydrogen phosphate (KH$_2$PO$_4$), sodium dihydrogen phosphate (NaH$_2$PO$_4$), dipotassium hydrogen phosphate (K$_2$HPO$_4$), disodium hydrogen phosphate (Na$_2$HPO$_4$), potassium phosphate (K$_3$PO$_4$), and sodium phosphate (Na$_3$PO$_4$).

8. The agent as set forth in claim 1, wherein the inorganic buffer system (b) consists of
   (b1) phosphoric acid (H$_3$PO$_4$) and
   (b2) at least one phosphate salt selected from the group consisting of potassium dihydrogen phosphate (KH$_2$PO$_4$) and sodium dihydrogen phosphate (NaH$_2$PO$_4$),
   with the agent that includes the inorganic acid (131) and the salt or salts of the inorganic acid (b2) being in a molar ratio (b1)/(b2) from 1:5 to 5:1.

9. The agent as set forth in claim 1, wherein agent is free of the organic carboxylic acids with 1 to 8 carbon atoms, such that the total of all the organic carboxylic acids with 1 to 8 carbon atoms in the agent is less than 0.05 weight percent, with respect to the total weight of the agent.

10. The agent as set forth in claim 1, wherein
    (d) the agent is free of all acids from the group of citric acid, lactic acid, malic acid, maleic acid, tartaric acid, glycolic acid, succinic acid, fumaric acid, malonic acid, oxalic acid, mandelic acid and the salts of these acids, such that a total content of all of the acids from the group of citric acid, lactic acid, malic acid, maleic acid, tartaric acid, glycolic acid, succinic acid, fumaric acid, malonic acid, oxalic acid, mandelic acid and the salts of these acids included in the agent—with respect to the total weight of the agent—lies below 0.5 wt %.

11. The agent as set forth in claim 1, wherein the agent has a pH value in the range from 1.0 to 5.5.

12. The agent as set forth in claim 1, further including
    (e) at least one solvent selected from the group consisting of propylene carbonate, benzyl alcohol, 2-phenoxyethan-1-ol, and benzyl alcohol.

13. The agent as set forth in claim 1, wherein the water (c) includes water with a degree of hardness (° dH) of at least 7.3, with the degree of hardness being calculated according to the following formula (mg calcium and magnesium per liter of water):

° dH=0.14×[Ca value in mg/1]+0.23×[Mg value in mg/1].

14. The agent as set forth in claim 1, further including
(f) one or more other propellant gases selected from the group consisting of dimethyl ether, propane, propene, n-butane, iso-butane, iso-butene, n-pentane, pentene, iso-pentane, and iso-pentene.

15. A cosmetic product comprising;
a cosmetic agent, wherein the cosmetic agent comprises at least one direct dye, an inorganic buffer system comprising at least one inorganic acid (b1) and at least one inorganic salt of this acid or these acids (b2), and water, and wherein;
the cosmetic agent is free of organic carboxylic acids with 1 to 8 carbon atoms, such that a total of all organic carboxylic acids with 1 to 8 carbon atoms in the cosmetic agent is less than 0.5 weight percent, with respect to a total weight of the cosmetic agent; and wherein;
the cosmetic agent is packed in a pressurized aerosol container, with the pressurized aerosol container having an aerosol dispensing device with spray valve.

16. A method for increasing the nuance stability of colorants, including applying to the keratinic fibers a mixture that includes
(a) at least one direct dye, and
(b) water, mixed with
an inorganic buffer system consisting of at least one inorganic acid (b1) and at least one inorganic salt of this acid or these acids (b2), and wherein;
the mixture is free of organic carboxylic acids with 1 to 8 carbon atoms, such that a total of all organic carboxylic acids with 1 to 8 carbon atoms in the mixture is less than 0.5 weight percent, with respect to a total weight of the mixture.

\* \* \* \* \*